United States Patent [19]

Siekmann

[11] Patent Number: 5,050,625
[45] Date of Patent: Sep. 24, 1991

[54] DENTAL FLOSS THREADING DEVICE

[75] Inventor: John D. Siekmann, Waukegan, Ill.

[73] Assignee: Plastisonics, Inc., Chicago, Ill.

[21] Appl. No.: 598,534

[22] Filed: Oct. 16, 1990

[51] Int. Cl.$^5$ ............................................. A61C 15/00
[52] U.S. Cl. ..................................... 132/323; 132/329
[58] Field of Search ............... 132/321, 323, 324, 329;
606/223, 224, 225; 223/102

[56] References Cited

U.S. PATENT DOCUMENTS

| | | | |
|---|---|---|---|
| 407,362 | 7/1889 | Mason . | |
| 1,210,205 | 12/1916 | Richardson . | |
| 1,608,212 | 11/1926 | Hochstadter . | |
| 3,779,256 | 12/1973 | Maloney et al. | 132/93 |
| 3,929,144 | 12/1975 | Tarrson et al. | 132/93 |
| 4,011,658 | 3/1977 | Tarrson et al. | 32/40 R |
| 4,064,883 | 12/1977 | Oldham | 132/321 |
| 4,133,339 | 1/1979 | Naslund | 132/323 |
| 4,215,478 | 8/1980 | Thomas et al. | 132/323 |
| 4,342,324 | 8/1982 | Sanderson | 132/92 R |
| 4,657,034 | 4/1987 | Koski | 132/92 R |
| 4,832,063 | 5/1989 | Smole | 132/321 |

Primary Examiner—Cary E. Stone
Attorney, Agent, or Firm—Trexler, Bushnell, Giangiorgi & Blackstone, Ltd.

[57] ABSTRACT

A device, a method of using such a device and a method for making such a device for threading floss between dental structures. The threading device is formed of a tube including a handle portion and a blade-like portion. A charge of dental floss is retained in the tube of which a lead portion extends through a tip aperture formed at a terminal tip or end of the blade-like portion. The lead portion is coated with a material to stiffen the same to further facilitate insertion of the device between dental structures. The device is formed by providing a tube and inserting a charge of floss therein. The tube and floss materials have different melting points such that the melting point for the floss material is greater than the melting point for the tube material. The tube is heated to its respective melting point whereupon a portion of the tube is formed into the blade-like portion. During the forming process, the lead portion of the floss is retained in place such that upon completion, it extends through the tip aperture.

12 Claims, 2 Drawing Sheets

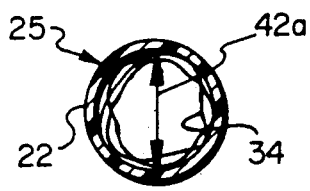
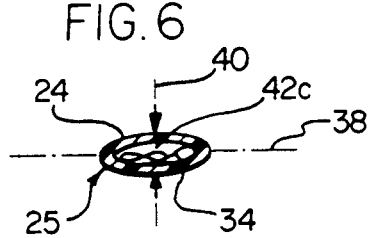
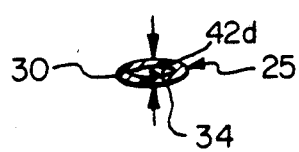
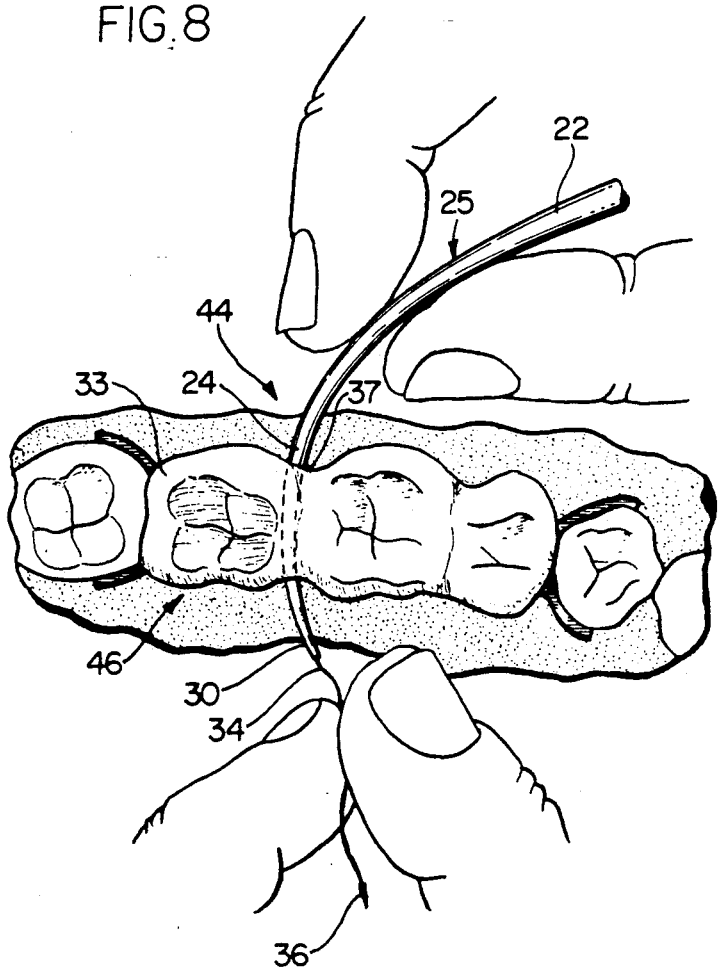
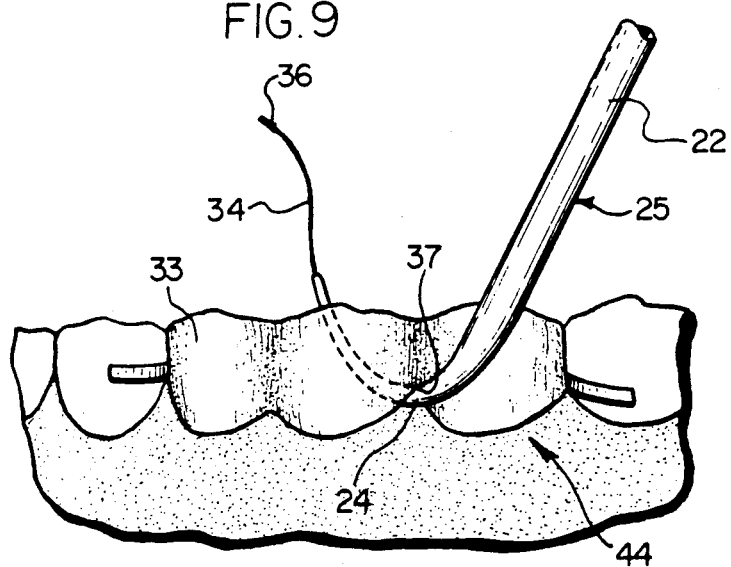

DENTAL FLOSS THREADING DEVICE

BACKGROUND OF THE INVENTION

The present invention relates to the dental floss threader arts, including a novel and improved dental floss threader, a method for making such a dental floss threader and methods of dental flossing using such a dental floss threader.

Dental floss is highly recommended and widely used in oral hygiene for cleaning areas and surfaces between abutting dental structures such as teeth, prosthetics and orthodontic devices. When used between teeth, dental floss is typically worked downwardly from a top surface of the teeth toward the gum line between abutting or adjacent surfaces. Once the floss is inserted between adjacent or abutting teeth, it is worked back and forth along each surface to remove undesirable particles and substances.

While it is generally uncomplicated to floss between teeth where at least a nominal space is available to insert a piece of floss, it is very difficult to insert floss between teeth which are tightly abutting or between prosthodontics such as artificial teeth or bridge work. Further, it is essentially impossible to insert a single thread of floss underneath such prosthodontic devices without the aid of a threading device.

Attempts to provide threading devices to insert floss between tight spaces or under prosthodontic devices have generally produced needle-like devices through which floss is threaded. These needle-like devices are inserted through any available gap between or near the structures to be flossed and then completely pulled through the gap in order to feed the floss through.

While typical prior art devices arguably provide a method of threading dental floss, they are often difficult to use and tend not to achieve their purpose. Many prior art floss threaders require regimens and if the regimen requires effort on the part of the user the user tends to not follow the regimen ultimately resulting in the failure of the device. For example, a device for inserting dental floss through interproximal areas is shown in U.S. Pat. No. 3,929,144 to Tarrson et al. and U.S. Pat. No. 4,011,658 to Tarrson et al. The device shown in the Tarrson et al. patents is essentially a needle having an enlarged loop at the end thereof. Dental floss must be inserted into the loop by the user prior to threading the floss into interproximal areas. This type of device thus requires additional effort and preparation on the part of the user and therefore tends to discourage use of the device as frequently as may be desirable.

Further, a device as shown in the Tarrson et al. patents requires that the user keep on hand both a supply of needle-like floss threading devices as well as floss. As an additional matter, some areas may be too small or confined to permit insertion of the needle-like device and the large loop. Such small areas may, therefore, be neglected when flossing, leading to potential oral hygiene complications.

Other attempts to resolve the problems of flossing as noted above are not believed to have succeeded. For example, one prior art solution was to coat the tip of predetermined lengths of floss with a material to make the tip rigid. This was believed to permit insertion of the floss itself in a needle-like manner between dental structures including very small spaces. However, due to the nature of dental floss, it is difficult to provide a sufficiently stiff coating to structurally support direct insertion between dental structures.

OBJECTS AND SUMMARY OF THE INVENTION

It is an object of the present invention to provide a floss threading device which permits insertion of dental floss between dental structures.

A related object is to provide a dental floss threader which has a rigid structure which permits insertion of dental floss into gaps between dental structures.

Yet another object of the present invention is to provide a novel method of threading floss between dental structures.

Still another object of the present invention is to provide a method of forming a floss threader having a charge of floss retained in a tube which is formed with a reduced diameter portion insertable between dental structures.

Briefly, and in accordance with the foregoing, the present invention comprises a device, a method of use and a method for making such a device, for threading floss between dental structures. The device is formed of a tube including a handle portion and a reduced diameter portion. A charge of dental floss is retained in the tube of which a lead portion extends through a tip aperture formed at a terminal end or tip of the reduced diameter portion. The lead portion is coated with a material to stiffen the same to further facilitate insertion of the device between dental structures. The device is formed by providing a tube and inserting a charge of floss therein. The tube and floss have different melting points such that the melting point for the floss is greater than the melting point for the tube material. The tube is heated to approximately the melting point of the tube material whereupon a portion of the tube is formed into the reduced diameter portion. During the forming process, the lead portion of the floss is retained in place such that upon completion, it extends through the tip aperture.

BRIEF DESCRIPTION OF THE DRAWINGS

The organization and manner of the operation of the disclosed embodiment of the present invention, together with further objects and advantages thereof, may be understood best by reference to the following description taken in connection with the accompanying drawings wherein like reference numerals identify like elements in which:

FIG. 4 is an enlarged transverse cross-sectional view of a handle portion of the threading device taken along 4—4 in FIG. 3;

FIG. 5 is an enlarged transverse cross-sectional view of a neck portion of the threading device taken along line 5—5 in FIG. 3 showing a reduction in a diameter of the threader;

FIG. 6 is an enlarged transverse cross-sectional view of a blade portion of the threading device taken along line 6—6 in FIG. 3;

FIG. 7 is an enlarged transverse cross-sectional view of a tip portion taken along line 7—7 in FIG. 3;

FIG. 8 is a plan view of the threading device of the present invention employed in inserting dental floss under a bridge work; and FIG. 9 is a side view of the threading device inserting dental floss under a portion of the bridge work shown in FIG. 8.

DESCRIPTION OF THE ILLUSTRATED EMBODIMENT

Figure 1:
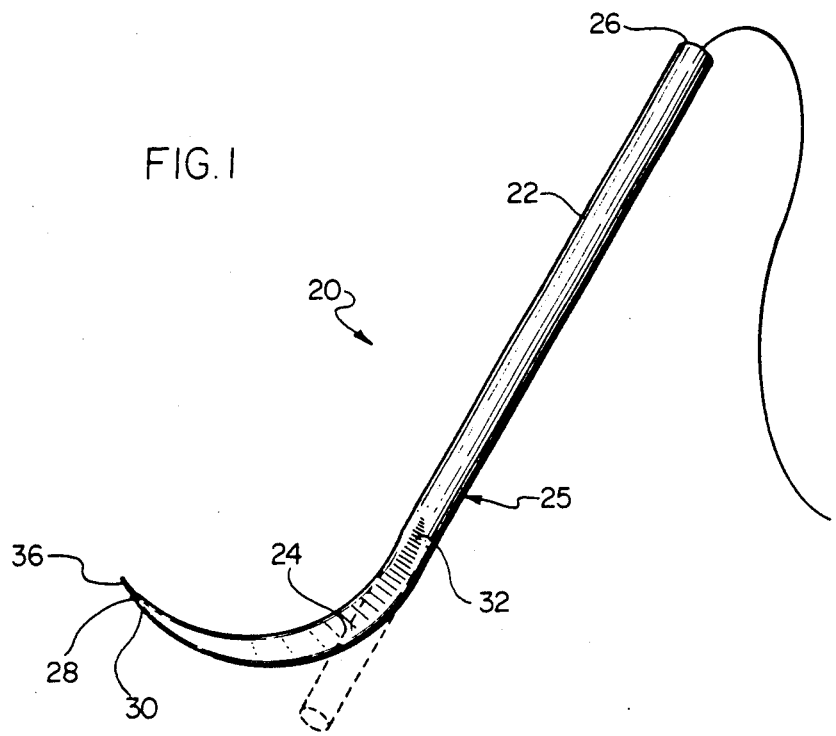
FIG. 1 is a perspective view of a dental floss threading device of the present invention containing a charge of dental floss therein.

While this invention may be susceptible to embodiment in different forms, a preferred embodiment is shown in the drawings and described herein in detail with the understanding that the present disclosure is to be considered an exemplification of the principles of the invention and is not intended to limit the invention to the embodiment illustrated and described herein.

It should be noted that dimensional relationships of the illustrated embodiment may vary in practice or may have been varied in the illustrations to emphasize certain features of the invention.

Referring now to the drawings wherein like parts are designated by the same reference numerals throughout the figures, a threading device 20 is shown in FIG. 1. The threading device 20 is formed of a hollow tube comprising a handle portion 22 and a curved reduced diameter, somewhat flattened portion or blade-like portion 24. Preferably, the threading device 20 is formed from a cylindrical, open-ended tube 25 partially shown in phantom line in FIG. 1. In an end of the handle 22 distal the blade-like portion 24 a fill aperture 26 is located at a terminal end or blade-like portion 24. A tip portion 30 is formed having a tip aperture 28 therethrough. A neck portion 32 is defined between the handle 22 and the blade-like portion 24 when the blade is formed thereon.

Figure 2:
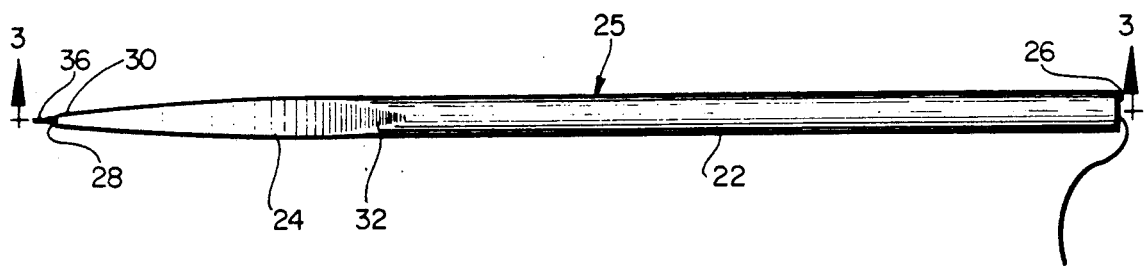
FIG. 2 is a plan view of the threading device as shown in FIG. 1.

As shown in FIG. 1, the blade-like portion 24 is preferably curved to facilitate insertion between dental structures 33 in difficult-to-reach places. As shown in FIG. 2, however, the threading device 20 is generally straight. The tubular columnar handle 22 of the threading device 20 generally exhibits more rigidity than the blade-like portion 24, which has been flattened somewhat during the forming process, and is generally more flexible. Moreover, increasing or decreasing the degree of curvature of portion 24 during formation, as compared to the illustrated curvature, is within the scope of the invention.

Figure 3:
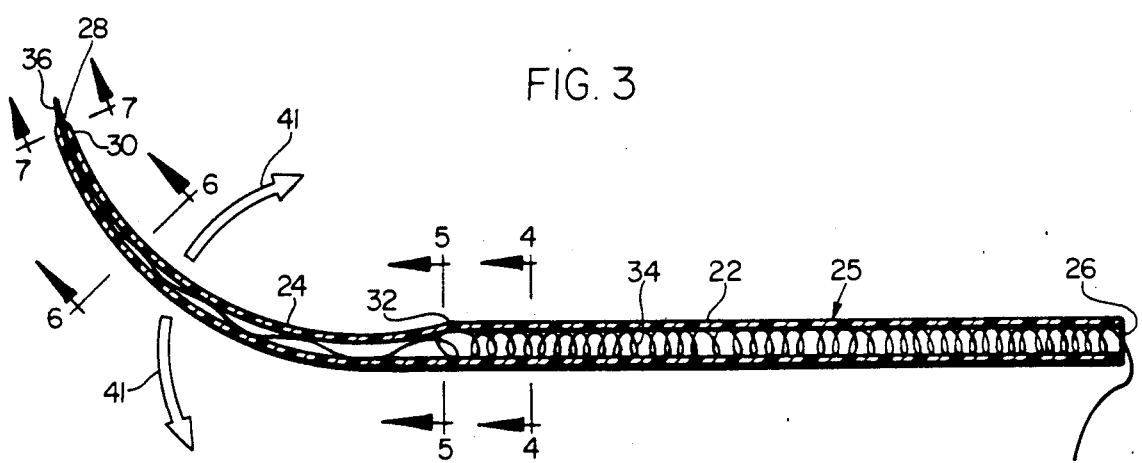
FIG. 3 is a cross-sectional side view of the threading device taken along line 3—3 in FIG. 2.

FIG. 3 provides a cross-sectional view of the threading device 20 illustrating a charge of floss 34 retained therein. Generally, the floss 34 retained in the handle portion 22 is coiled in order to accommodate a predetermined length of floss 34 which is longer than the overall length of the threading device 20, into the threading device 20. At approximately the neck portion 32, the floss 34 is no longer coiled and instead is a generally linear portion of floss extending through the blade-like portion 24 and protruding through the tip aperture 28 formed through the tip portion 30. A lead portion 36 of the floss extends beyond the tip portion 30 and is preferably coated with a substance for stiffening the same. The entire floss may be so coated if desired. The coated stiffened lead portion 36 facilitates insertion of the threading device 20 through small areas 37 between dental structures 33 as heat viewed in FIGS. 8 and 9. Further, the lead portion 36 provides a gripping portion for pulling floss 34 from the threading device 20.

FIGS. 4–7 illustrate transverse cross-sections of the threading device 20 taken along the respective section lines as illustrated in FIG. 3. As shown in FIG. 4, the handle portion 22 has a generally circular cross-section providing strength and rigidity to the device. FIG. 5 illustrates the neck portion 32 in which the generally circular cross-section of the handle 22 has been flattened. FIG. 6 illustrates a cross-section taken through the blade-like portion 24 in which the diameter of the tube (see diameters 42a, 42b, 42c and 42d in FIGS. 4–7, respectively) has been substantially reduced or flattened and drawn. In the cross sectional view of FIG. 6, the blade-like portion 24 has a major axis 38 and a minor axis 40. The blade-like portion 24 is generally inflexible when forces are applied perpendicular to the minor axis 40 but is flexible when forces are applied perpendicular to the major axis 38 (as indicated by arrows 41 in FIG. 3). This flexibility, or inflexibility, functions to enhance the control of the threading device 20 when used. In FIG. 7, a cross-section is taken through the tip portion 30.

The present invention further includes a method of forming a dental floss threading device 20. The tube, from which the handle 22 and blade-like portion 24 are formed, is formed of a material having a first melting temperature. The floss material having a second melting temperature which is greater than the first melting temperature, that of the tube.

In forming the threading device 20, a tube 25 is provided and a charge of floss 34 is inserted therein. A lead portion 36 of the floss 34 is retained extending from one end of the tube 25 throughout the forming process. The tube 25 is heated to approximately the first melting temperature such that the tube 25 may be formed. At least a portion of the heated portion of the tube 25 is drawn into the blade-like portion 24 while retaining the lead portion 36 extending therefrom. The blade-like portion 24 formed as such, is formed into a desired curvature shape and retained in such shape during a cooling process. A substance may be applied to the lead portion 36 of the floss 34 to stiffen the portion for facilitating insertion of the lead portion 36 into small gaps 37 between dental structures 33.

As a further component of the invention, a novel method of threading dental floss between dental structures 33 for cleaning therebetween is provided. This novel method of threading dental floss includes providing a tube 25 with a handle portion 22 and a blade-like portion 24 having a charge of floss 34 retained therein. The tube 25 is provided with a curved blade-like portion 24 and has a projecting lead portion 36 of the floss 34 which has preferably been coated with a stiffening substance to promote insertion thereof, and of the following tip portion 30 of the threader between dental structures 33.

With reference to FIGS. 8 and 9, the method of threading dental floss is shown. The floss 34, retained inside of the tube 25 as described hereinabove, is to be inserted between dental structures from a first side 44 and a lead portion 36 (see also, FIG. 1) is driven underneath or between the dental structures 33 until at least the tip of the tube projects from a second side 46 (see, FIGS. 8 and 9). Once a part of the tube 25, and the lead portion 36 extending therefrom, extend from the second side 46 the lead portion 36 is grasped to extract the floss 34 from the tube 25 thereby permitting movement of the floss 34 against the abutting surfaces on the sides of the gap 37 through which the tube 25 has been inserted. In this method of threading dental floss 34 between dental structures 33 it is useful to provide a tube 25 with a curved portion 24 and preferably having a reduced diameter to facilitate insertion of the tube 25 into a gap 37 between dental structures 33. Further, it is preferable to provide a tube 25 which has a relatively rigid handle portion 22 so that only one hand needs to be used to manipulate the tube 25 while inserting a tip portion 30 into a gap 37. The tip and/or blade-like portion 24 may be made relatively flexible to permit access to confined areas.

While a particular embodiment of the present invention has been shown and described in detail herein, it may be obvious to those skilled in the art that changes and modifications of the present invention in its various aspects, may be made without departing from the invention in its broader aspects, some of which changes and modifications being matters of routine engineering or design, and others being apparent after study. As such, the scope of the invention should not be limited by the particular embodiment and specific construction described herein, but should be defined in the appended claims and equivalents thereof. Accordingly, the aim of the appended claims is to cover all such changes and modifications as all within the true spirit and scope of the invention.

The invention is claimed as follows:

1. A threading device for inserting dental floss between dental structures for cleaning therebetween, said device comprising: an elongated tube into which a charge of floss of a predetermined length is loaded, said tube including an integrally formed handle portion and a reduced diameter portion; said handle portion being dimensioned for containing said charge of floss, a fill aperture formed in said handle portion for receiving said floss therethrough; said reduced diameter portion integrally formed on an end of said handle portion distal said fill aperture for insertion between dental structures; a threading tip formed on an end of said reduced diameter portion distal said handle portion having a tip aperture formed in an end thereof through which a lead portion of said charge of floss projects.

2. A threading device according to claim 1, wherein said handle portion is a generally tubular column for resisting deflection of said handle portion such that said device may be inserted between dental structures using a single hand.

3. A threading device according to claim 1, wherein said reduced diameter portion is formed with a major axis and a minor axis defining a cross-sectional area thereof, said reduced diameter portion being deflectable in a generally curved path defined by the major axis perpendicular to a plane formed by the minor axis.

4. A threading device according to claim 1, wherein said reduced diameter portion defines a blade-like portion intermediate said handle portion and said threading tip, said blade-like portion being formed curved relative to an axis defined by said handle portion.

5. A threading device according to claim 4, wherein said blade-like portion is resiliently deflectable for increasing and decreasing the degree of relative curvature of the blade-like portion to facilitate insertion of the threading tip and lead portion of the floss between dental structures.

6. A threading device according to claim 1, wherein said lead portion of said charge of floss which projects through said tip aperture is coated with a predetermined substance for stiffening the lead portion to promote insertion between dental structures.

7. A method of threading dental floss between dental structures for cleaning therebetween comprising the steps of: integrally forming a tube having a handle portion and a threading tip portion having a tip aperture therethrough; inserting a charge of a predetermined length of dental floss inside of said tube; extending a lead portion of said charge of floss through said tip aperture formed through said tip portion; inserting said lead portion of said floss and said tip portion of said tube between dental structures from a first side of said dental structures; and grasping said lead portion on a second side of said dental structures and extracting a portion of said charge of floss from said tube and between said dental structures.

8. A method according to claim 7, further including the step of coating said lead portion of said charge of floss for stiffening said lead portion to facilitate insertion of said lead portion between dental structures.

9. A threading device for inserting dental floss between abutting dental structures, said device comprising: a hollow tube having a generally straight handle portion and a curved blade-like portion extending from said handle portion, said handle portion being relatively stiff and said curved blade-like portion being relatively flexible, said curved blade-like portion being flattened for facilitating insertion thereof between dental structures, said blade-like portion terminating in a tip portion having a tip aperture formed therethrough; a charge of dental floss retained in said hollow tube, a lead portion of said charge of floss extending through said tip aperture, said lead portion being coated with a material for stiffening the lead portion for facilitating insertion of said lead portion between dental structures.

10. A method of making a threading device for threading dental floss between dental structures comprising the steps of: providing a tube formed of a material having a first melting temperature; inserting a charge of dental floss into said tube with a lead portion of said floss extending from one end of said tube, said dental floss being formed of a material having a second melting temperature greater than said first melting temperature; heating a portion of said tube to said first melting temperature; drawing at least a portion of said heated portion of said tube into a blade-like portion retaining said lead portion extending therefrom; cooling said heated portion to retain the shape of the blade-like portion formed therein.

11. A method according to claim 10, further including the steps of: curving said tube while forming said blade-like portion; and retaining said curve upon cooling said heated portion to retain a curved shape of said blade-like portion.

12. A method according to claim 10, further including the steps of: coating the lead portion of the charge of floss to stiffen the lead portion for facilitating insertion of said lead portion between dental structures.

* * * * *